United States Patent
Majeed et al.

(10) Patent No.: US 10,323,227 B2
(45) Date of Patent: Jun. 18, 2019

(54) PROCESS FOR ENHANCING THE VIABLE COUNTS OF LACTIC ACID BACTERIA AND USEFUL COMPOSITIONS THEREOF

(71) Applicants: Muhammed Majeed, Edison, NJ (US); Kalyanam Nagabhushanam, East Windsor, NJ (US); Sivakumar Arumugam, Bangalore (IN); Furqan Ali, Bangalore (IN)

(72) Inventors: Muhammed Majeed, Edison, NJ (US); Kalyanam Nagabhushanam, East Windsor, NJ (US); Sivakumar Arumugam, Bangalore (IN); Furqan Ali, Bangalore (IN)

(73) Assignee: SAMI LABS LIMITED, Bangalore (IN)

(*) Notice: Subject to any disclaimer, the term of this patent is extended or adjusted under 35 U.S.C. 154(b) by 0 days.

(21) Appl. No.: 15/661,218

(22) Filed: Jul. 27, 2017

(65) Prior Publication Data
US 2017/0327785 A1    Nov. 16, 2017

Related U.S. Application Data

(63) Continuation-in-part of application No. 15/622,616, filed on Jun. 14, 2017, which is a continuation-in-part of application No. 14/839,923, filed on Aug. 29, 2015, now Pat. No. 9,717,766.

(60) Provisional application No. 62/063,453, filed on Oct. 14, 2014, provisional application No. 62/043,599, filed on Aug. 29, 2014.

(51) Int. Cl.
| | |
|---|---|
| C12N 1/20 | (2006.01) |
| C12P 7/52 | (2006.01) |
| C12P 7/54 | (2006.01) |
| C12P 7/64 | (2006.01) |
| A61K 35/00 | (2006.01) |
| A61K 35/742 | (2015.01) |

(52) U.S. Cl.
CPC .............. *C12N 1/20* (2013.01); *A61K 35/742* (2013.01); *C12P 7/52* (2013.01); *C12P 7/54* (2013.01); *C12P 7/6409* (2013.01); *A61K 2035/115* (2013.01)

(58) Field of Classification Search
CPC ............ C12N 1/20; C12P 7/6409; C12P 7/54; C12P 7/52; A61K 35/742; A61K 2035/11
See application file for complete search history.

(56) References Cited

U.S. PATENT DOCUMENTS

2003/0147857 A1* 8/2003 Monte .................. A61K 35/745
424/93.4

OTHER PUBLICATIONS

Han et al., Food Funct., 2014, vol. 5, p. 2446-2452.*
Nutra "Probiotics for Health and Well Being", 2007, by Majeed and Prakash 14 pages of PDF.*
Stig Bengmark and Robert Martindale. "Probiotics and Synbiotics in Clinical Medicine". Nutr Olin Pract vol. 20 244-261, Apr. 2005.
Gabriella A. Varga and Eric S. Kolver, "Microbial and Animal Limitations to Fiber Digestion and Utilization", J. Nutr. May 1, 1997 vol. 127 No. 5 819S-823S.
Guidelines for the evaluation of probiotics in food, Joint FAO/WHO Working Group Report on Drafting Guidelines for the Evaluation of Probiotics in Food, London, Ontario, Canada, Apr. 30 and May 1, 2002.
Probiotics: In Depth/NCCIH, U.S. Department of Health and Human Services (http://www.hhs.gov/) National Institutes of Health (http://www.nih.gov/); , 2015.
Indian Council of Medical Research/Department of Biotechnology, Ministry of Science and Technology, Government of India, New Delhi), ICMR-DBT Guidelines for Evaluation of Probiotics in Food, 2011).
New study finds ProDURA Bacillus coagulans Demonstrates Superior heat resistance, University of Nebraska, http://valentuschoice.com/ProDura-Comparison.pdf, accessed on Sep. 24, 2018.
Mannu et al., "Comparison of the incidence of virulence determinants and antibiotic resistance between Enterococcus strains of dairy, animal and clinical origin", International Journal of Food Microbiology (2003); 88:291-304.
Muralitharan & Thajuddin, Rapid differentiation of phenotypically and genotypically similar Synechococcus elongatus by PCR fingerprinting, 2011, Biologia 66/2: 238-243, DOI: 10.2478/s11756-011-0003-82011.

* cited by examiner

*Primary Examiner* — Kade Ariani

(57) ABSTRACT

Disclosed herein is a composition containing turmeric starch for use as a prebiotic plant fiber. Also disclosed is a method to increase the viable counts of *Bacillus coagulans* MTCC 5856 by co-culturing with turmeric starch and the production of short chain fatty acids (SCFA) by *Bacillus coagulans* MTCC 5856 using turmeric starch.

5 Claims, 8 Drawing Sheets

PROCESS FOR ENHANCING THE VIABLE COUNTS OF LACTIC ACID BACTERIA AND USEFUL COMPOSITIONS THEREOF

CROSS-REFERENCE TO RELATED APPLICATIONS

This application is a continuation of U.S. patent application Ser. No. 15/622,616 filed on Jun. 14, 2017, which is a continuation of U.S. patent application Ser. No. 14/839,923, filed on Aug. 29, 2015, which in turn claims the benefit of priority to U.S. Provisional Application No. 62/043,599, filed on Aug. 29, 2014, and 62/063,453, filed on Oct. 14, 2014. The disclosure of the prior applications is hereby incorporated by reference herein in its entirety.

BACKGROUND

Field of the Invention

The invention in general relates to *Bacillus coagulans* (Lactic acid bacteria). More specifically, the invention relates to (i) the growth promotional activity of natural plant based fibers on *Bacillus coagulans* MTCC 5856; (ii) The production of short chain fatty acids (SCFA) by *Bacillus coagulans* MTCC 5856 using plant based natural fibers; and (iii) the combination of natural plant based fibers and *Bacillus coagulans* MTCC 5856 to inhibit Gram Negative pathogenic bacteria.

Description of Prior Art

Combining multistrain probiotics (probiotic bacteria) and prebiotics to achieve enhanced immunosupportive effects is well known in the art. Specifically combining probiotics with natural plant based fibers to formulate synbiotics is reported as a promising therapeutic approach (Stig Bengmark and Robert Martindale. "Prebiotics and Synbiotics in Clinical Medicine". Nutr Clin Pract vol 20 244-261, April 2005). The success of such an approach depends on carefully choosing specific probiotic microorganisms whose viable count is effectively enhanced by natural plant based fibers that are resistant to both enzymatic and acid hydrolysis in the gut. These studies are critically important to accommodate the performance of host animals exposed to symbiotic diet regimes given the teaching that there are limitations to fiber digestion and utilisation by microbes in terms of microbial accessibility to substrates, physical and chemical nature of fibers (forage) and also kinetics of the digestive process (Gabriella A. Varga and Eric S. Kolver, "Microbial and Animal Limitations to Fiber Digestion and Utilization", J. Nutr. May 1, 1997 vol. 127 no. 5 819S-823S).

It is the principle objective of the present invention to evaluate the performance of selected natural fibers (enzyme and acid hydrolysis resistant) to enhance the viable counts of *Bacillus coagulans* MTCC 5856.

It is also another objective of the present invention to evaluate the ability of the synbiotic composition (natural fibers and *Bacillus coagulans* MTCC 5856) to inhibit pathogenic Gram negative bacteria.

It is yet another objective of the present invention to evaluate the ability of the synbiotic composition (natural fibers and *Bacillus coagulans* MTCC 5856) to produce desired short chain fatty acids, said property having profound therapeutic applications.

The present invention fulfils the aforesaid objectives and provides further related advantages.

Deposit of Biological Material

The deposit of biological material *Bacillus coagulans* bearing accession number MTCC 5856, mentioned in the instant application has been made on 19 Sep. 2013 at Microbial Type Culture Collection & Gene Bank (MTCC), CSIR-Institute of Microbial Technology, Sector 39-A. Chandigarh—160036, India.

SUMMARY

Disclosed is (i) the growth promotional activity of natural plant based fibers on *Bacillus coagulans* MTCC 5856; (ii) the combination of natural plant based fibers and *Bacillus coagulans* MTCC 5856 to inhibit Gram negative pathogenic bacteria and (iii) the production of short chain fatty acids (SCFA) by *Bacillus coagulans* MTCC 5856 using plant based natural fibers.

Other features and advantages of the present invention will become apparent from the following more detailed description, taken in conjunction with the accompanying images, which illustrate, by way of example, the principle of the invention.

DETAILED DESCRIPTION

Figure 1A:
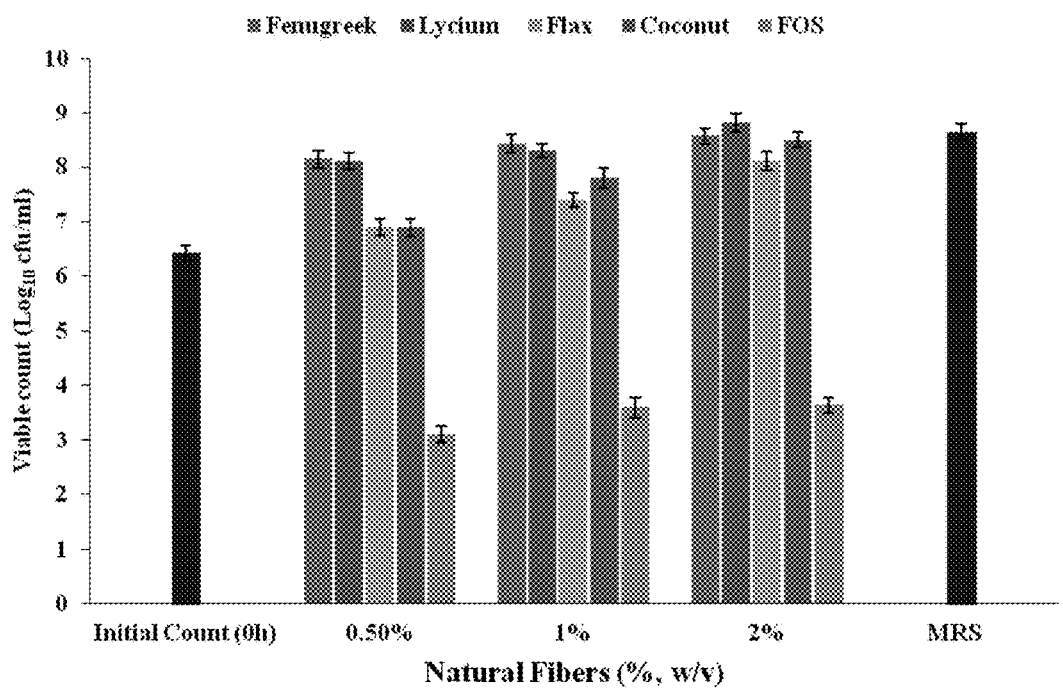
FIGS. 1A, 1B and IC show the graphical representation of the increase in viable colony count of *Bacillus coagulans* MTCC 5856 in presence of different natural plant fibers alone (%, w/v).

In the most preferred embodiment, the present invention relates to a method of increasing the viable colony count of *Bacillus coagulans* MTCC 5856 said method comprising step of growing *Bacillus* coagulant MTCC 5856 in the presence of natural plant fibers selected from the group consisting of *Trigonella foenum-graecum* (fenugreek) seed fibers, *Lycium barbarum* seed fibers, *Linum usilatissimum* (Flax) seed fibers, *Cocos nucifera* (Coconut) fibers, *Zingiber officinale* (Ginger) rhizome fibers, *Emblica officinals* (Amla) fruit fibers, *Plantago ovata* (*Psyllium*) fibers and *Vaccinium oxycoccos* (Cranberry) seed fibers.

In another most preferred embodiment, the present invention relates to a method of inhibiting pathogenic Gram negative bacteria said method comprising step of bringing to contact said Gram negative bacteria with *Bacillus coagulans* MTCC 5856 co-cultured with natural plant fibers selected from the group consisting of *Trigonella foenum-graecum* (fenugreek) seed fibers, *Lycium barbarum* seed fibers, *Linum usitatissimum* (Flax) seed fibers, *Cocos nucifera* (Coconut) fibers, *Zingiber officinale* (Ginger) rhizome fibers, *Emblica officinalis* (Amla) fruit fibers, *Plantago ovata* (*Psyllium*) fibers and *Vaccinium oxycoccos* (Cranberry) seed fibers.

In yet another most preferred embodiment, the present invention also relates to a method of producing short chain fatty acids by co-culturing *Bacillus coagulans* MTCC 5856 with natural plant fibers selected from the group consisting of *Trigonella foenum-graecum* (fenugreek) seed fibers, *Lycium barbarum* seed fibers, *Linum usitatissimum* (Flax) seed fibers, *Cocos nucifera* (Coconut) fibers, *Zingiber officinale* (Ginger) rhizome fibers, *Emblica officinalis* (Amla) fruit fibers, *Plantago ovata* (*Psyllium*) fibers and *Vaccinium oxycoccos* (Cranberry) seed fibers. In alternate embodiments, the present invention also relates to a method of protecting against diet-induced obesity and insulin resistance in the mammalian gut by administering composition comprising *Bacillus coagulans* MTCC 5856 with natural plant fibers selected from the group consisting of *Trigonella foenum-graecum* (fenugreek) seed fibers, *Lycium barbarum* seed fibers, *Linum usitatissimum* (Flax) seed fibers, *Cocos nucifera* (Coconut) fibers, *Zingiber officinale* (Ginger) rhizome fibers, *Emblica officinalis* (Amla) fruit fibers, *Plantago ovata* (*Psyllium*) fibers and *Vaccinium oxycoccos* (Cranberry) seed fibers to bring about the effect of protection against diet induced obesity and insulin resistance.

In another most preferred embodiment, the invention discloses a composition containing turmeric starch for use as a prebiotic plant fiber. In a related embodiment, the turmeric starch is isolated from the spent rhizomes of *Curcuma longa*.

In an another preferred embodiment, the invention discloses a method comprising co-culturing *Bacillus coagulans* with turmeric starch fibres, wherein the viable colony count of *Bacillus coagulans* is increased by the co-culturing method.

In an another preferred embodiment, the invention discloses a method of producing short chain fatty acids, comprising performing the method of co-culturing *Bacillus coagulans* with turmeric starch fibres under fermenting conditions to produce short chain fatty acids. In a related embodiment, the short chain fatty acids are one or more selected from the group consisting of acetic acid, propionic acid, and butyric acid. In another related embodiment, the *Bacillus coagulans* and the turmeric starch are fermented under anaerobic conditions.

In a preferred embodiment, the *Bacillus coagulans* is *Bacillus coagulans* MTCC 5856.

In an another preferred embodiment, the invention discloses a method comprising co-culturing *Bacillus coagulans* MTCC 5856 with turmeric starch fibres, wherein the viable colony count of *Bacillus coagulans* MTCC 5856 is increased by the co-culturing method.

In an another preferred embodiment, the invention discloses a method of producing short chain fatty acids, comprising performing the method of co-culturing *Bacillus coagulans* MTCC 5856 with turmeric starch fibres under fermenting conditions to produce short chain fatty acids. In a related embodiment, the short chain fatty acids are one or more selected from the group consisting of acetic acid, propionic acid, and butyric acid. In another related embodiment, the *Bacillus coagulans* MTCC 5856 and the turmeric starch are fermented under anaerobic conditions.

The specific examples included herein below illustrate the aforesaid most preferred embodiments of the present invention.

Example I

Method of Preparing Fibers

*Trigonella Foenum-Graecum* (Fenugreek) Seed Fibers

*Trigonella foenum-graecum* (also known as Fenugreek) seeds were collected from local market and milled to course powder (10 mesh pass through). Further, four volumes of n-hexane was added to 100 gm of *Trigonella foenum-graecum* seeds course powder and extracted at reflux temperature. n-Hexane fraction was filtered through Whatman filter no 1 and again three times same extraction was carried out. After extraction, retentate was dried at 80° C. for 5 h and then this was milled to obtain 40 mesh pass through powder. In an alternative method, fat or oil from Fenugreek seeds were removed by Super Critical fluid extraction method using liquid $CO_2$ as solvent. To increase the dietary fiber (Galactomannans) content, the enzymatic hydrolysis using Cellulase was carried out. The galactomannans content was determined by Megazyme kit (K-GALM 03/11) as per the manufacturer's instructions (Megazyme International Ireland, Bray Business Park, Bray, Co. Wicklow, IRELAND).

*Lycium barbarum* Seed Fibers

Goji, Goji berry or Wolfberry is the fruit of *Lycium barbarum*. The fruit of *Lycium barbarum* was dried and seeds were separated and milled to course powder. Further, four volumes of n-hexane was added to 100 gm of *Lycium barbarum* course powder and extracted at reflux temperature. n-Hexane fraction was filtered through Whatman filter no 1 and again three times same extraction was carried out. After extraction, retentate was dried at 80° C. for 5 h and then this was milled to obtain 60 mesh pass through powder. Total dietary fiber was determined by Enzymatic-Gravimetric Method (AOAC 985.29).

*Linum usitatissimum* (Flax Seed) Fibers

*Linum usitatissimum* (also known as common flax or linseed or Flax) seeds were collected and milled to course powder (10 mesh pass through). Further, four volumes of n-hexane was added to 100 gm of *Linum usitatissimum* course powder and extracted at reflux temperature. n-Hexane fraction was filtered through Whatman filter no 1 and again three times same extraction was carried out. After extraction, retentate was dried at 80° C. for 5 h and then this was milled to obtain 40 mesh pass through powder. Total dietary fiber was determined by Enzymatic-Gravimetric Method (AOAC 985.29).

*Cocos nucifera* Fibers

A matured coconut was procured from local market and dried. Further, the endosperm (coconut meat) was chopped to course and uniform size material. Further, four volumes of n-hexane was added to 100 gm of *Cocos nucifera* course material and extracted at reflux temperature. n-Hexane fraction was filtered through Whatman filter no 1 and again three times same extraction was carried out. After extraction, retentate was dried at 80° C. for 5 h and then this was milled to obtain 60 mesh pass through powder. Total dietary fiber was determined by Enzymatic-Gravimetric Method (AOAC 985.29).

*Zingiber officinale* (ginger) rhizome fibers

*Zingiber officinale* rhizome, ginger root or simply ginger was dried and milled to course powder (10 mesh pass through). Further, four volumes of n-hexane was added to 100 gm of *Zingiber officinale* rhizome course powder and extracted at reflux temperature. n-Hexane fraction was filtered through Whatman filter no 1 and again three times same extraction was carried out. In an alternative method, fat or oil from Fenugreek seeds were removed by Super Critical fluid extraction method using liquid $CO_2$ as solvent. After extraction, retentate was dried at 80° C. for 5 h and then this was milled to obtain 40 mesh pass through powder. Total dietary fiber was determined by Enzymatic-Gravimetric Method (AOAC 985.29).

*Emblica officinalis* (Amla) fruit fibers

*Emblica officinalis* (*Phyllanthus emblica*), also known as Emblic, Emblic myrobalan, Myrobalan, Indian gooseberry, Malacca tree, or Amla from Sanskrit Amalika. The fruit of *Emblica officinalis* was procured from local market and dried, pulverized and passed through 60 mesh. This powder was used for the extraction of fibers. Total dietary fiber was determined by Enzymatic-Gravimetric Method (AOAC 985.29).

Example 2—Acid Hydrolysis

Two grams of plant based natural fibers listed in Table 1 were dissolved in 100 ml of HCl (0.10 M) and incubated at 37° C. with 100 rpm for 180 min. Samples were taken at 0, 30, 60, 90, 120 and 180 min. Fructooligosaccharide (FOS; Tata Chemicals, India) was also taken in the study as reference to compare with natural fibers and starch (Potato soluble starch; HiMedia, Mumbai, India) was also taken as control. The increase in reducing carbohydrates was measured by Dinitrosalicylate reagent (Nilsson and Bjorck 1988. Journal of Nutrition 118, 1482-1486).

TABLE 1

Total dietary fiber content of plant based natural fibers

| S. No. | Natural Fibers | Dietary Fibers (%, w/w) | | |
|---|---|---|---|---|
| | | Soluble Fibers | Insoluble Fibers | Total |
| 1 | *Trigonella foenum-graecum* (Fenugreek) seed fibers | 65.42 ± 1.2 | 5.41 ± 0.4 | 75.24 ± 1.2 |
| 2 | *Lycium barbarum* seed fibers | ND | 38.05 ± 0.9 | 39.71 ± 1.1 |
| 3 | *Linum usitatissimum* (Flax) seed fibers | 34.68 ± 0.4 | 12.73 ± 0.1 | 50.21 ± 1.5 |
| 4 | *Cocos nucifera* (Coconut) fibers | 33.16 ± 0.7 | 36.16 ± 0.2 | 65.41 ± 1.7 |
| 5 | *Zingiber officinale* (Ginger) rhizome fibers | ND | 41.55 ± 0.7 | 42.18 ± 0.8 |
| 6 | *Emblica officinalis* (Amla) fruit fibers | 10.15 ± 0.2 | 41.58 ± 0.5 | 52.07 ± 1.4 |
| | Soluble Fraction | 19.04 ± 0.5 | 1.527 ± 0.1 | 22.29 ± 0.4 |
| | Insoluble Fraction | 27.05 ± 0.7 | 3.55 ± 0.1 | 33.03 ± 0.7 |
| 7 | *Plantago ovata* (Psyllium) Fibers | 51.13 ± 0.8 | 30.24 ± 0.8 | 83.24 ± 1.5 |
| 8 | *Vaccinium oxycoccos* (Cranberry) seed fibers | 10.21 ± 0.6 | 39.81 ± 07 | 51.92 ± 1.3 |

ND, Not detected; Total dietary fiber was determined by Enzymatic-Gravimetric Method (AOAC 985.29).

Table 2 shows the effect of acid hydrolysis on (0.1 M HCl; 37° C., 100 rpm) on Plant Based Natural Fibers. Total reducing sugar was determined by Dinitrosalicylic acid (DNSA) method.

TABLE 2

| | | Percentage of Total Reducing Sugar | | | | | |
|---|---|---|---|---|---|---|---|
| S. No. | Plant Based Natural Fibers | 0 min | 30 min | 60 min | 90 min | 120 min | 180 min |
| 1 | Fenugreek seed fibers | 3.79 ± 0.1 | 3.90 ± 0.1 | 3.95 ± 0.09 | 3.33 ± 0.1 | 4.22 ± 0.2 | 4.45 ± 0.1 |
| 2 | *Lycium barbarum* seed fibers | 11.91 ± 0.2 | 12.05 ± 0.2 | 12.98 ± 0.3 | 11.94 ± 0.4 | 12.98 ± 0.3 | 12.51 ± 0.2 |
| 3 | Flax seed fibers | 1.24 ± 0.1 | 1.89 ± 0.09 | 1.97 ± 0.1 | 2.10 ± 0.1 | 1.98 ± 0.1 | 2.21 ± 0.1 |
| 4 | Coconut Fiber | 6.11 ± 0.09 | 6.51 ± 0.2 | 7.25 ± 0.1 | 8.35 ± 0.2 | 9.95 ± 0.2 | 10.05 ± 0.5 |
| 5 | Ginger rhizome fibers | 4.02 ± 0.1 | 7.24 ± 0.5 | 7.98 ± 0.3 | 8.1 ± 0.7 | 7.8 ± 0.2 | 7.5 ± 0.3 |
| 6 | Amla Fruit Fiber (Soluble + Insoluble) | 16.59 ± 0.2 | 16.14 ± 0.7 | 16.84 ± 0.3 | 15.16 ± 0.4 | 17.12 ± 0.6 | 16.98 ± 0.6 |
| 7 | Amla Soluble Fiber | 19.96 ± 0.3 | 24.75 ± 0.5 | 24.13 ± 0.6 | 23.42 ± 0.7 | 22.76 ± 0.8 | 23.17 ± 0.5 |
| 8 | Amla Insoluble Fiber | 6.98 ± 0.1 | 6.74 ± 0.1 | 6.92 ± 0.2 | 6.95 ± 0.2 | 7.18 ± 0.1 | 7.60 ± 0.1 |
| 9 | Psyllium husk Fiber | 0.62 ± 0.01 | 1.11 ± 0.09 | 1.28 ± 0.04 | 1.42 ± 0.1 | 1.51 ± 0.1 | 1.62 ± 0.1 |
| 10 | Cranberry seed Fiber | 19.70 ± 0.4 | 19.15 ± 0.3 | 20.50 ± 0.9 | 19.76 ± 0.7 | 19.67 ± 0.9 | 20.60 ± 0.8 |
| 11 | Fructooligosaccharide (FOS) | 1.48 ± 0.1 | 6.29 ± 0.1 | 8.96 ± 0.1 | 9.63 ± 0.2 | 10.47 ± 0.2 | 12.52 ± 0.4 |
| 12 | Potato Soluble Starch | 7.60 ± 0.2 | 21.43 ± 0.2 | 21.03 ± 0.5 | 25.05 ± 0.7 | 27.11 ± 0.7 | 34.20 ± 0.3 |

Example 3—Enzymatic Hydrolysis 100 mg of Pancreatin from Porcine pancreas 4×USP (Sigma-Aldrich Corporation St. Louis Mo., USA) was dissolved in 100 ml of phosphate buffer (50 mM; pH 7.0). Further, plant based natural fibers (2 gm) were dissolved in above Pancreatin solution and incubated at 37° C. with 100 rpm for 180 min. Samples were taken at 0, 30, 60, 90, 120 and 180 min. FOS was also taken in the study as reference to compare with plant based natural fibers and starch was also taken as control. The increase in reducing carbohydrates was measured with a Dinitrosalicylate reagent (Oku et al. 1984. Journal of Nutrition 114, 1574-1581). The effect of enzymatic hydrolysis (0.1% Pancreatin in 20 mM PBS pH 7.0; 37° C., 100 rpm) on plant based natural fibers is represented in Table 3. Total reducing sugar was determined by Dinitrosalicylic acid (DNSA) method.

TABLE 3

| | | Percentage of total reducing sugar | | | | | |
|---|---|---|---|---|---|---|---|
| S. No. | Plant Based Natural Fibers | 0 min | 30 min | 60 min | 90 min | 120 min | 180 min |
| 1 | Fenugreek seed fibers | 7.20 ± 0.1 | 8.15 ± 0.1 | 11.85 ± 0.8 | 11.35 ± 0.8 | 10.55 ± 0.1 | 10.70 ± 0.2 |
| 2 | *Lycium barbarum* seed fibers | 11.86 ± 0.2 | 18.11 ± 0.8 | 17.85 ± 0.2 | 17.75 ± 0.4 | 17.53 ± 0.8 | 18.21 ± 0.4 |
| 3 | Flax seed fibers | 1.12 ± 0.1 | 2.56 ± 0.05 | 2.57 ± 0.1 | 2.98 ± 0.1 | 2.78 ± 0.08 | 2.88 ± 0.04 |
| 4 | Coconut Fiber | 8.85 ± 0.2 | 11.65 ± 0.2 | 14.25 ± 0.5 | 13.60 ± 0.2 | 10.90 ± 0.4 | 11.05 ± 0.08 |
| 5 | Ginger rhizome fibers | 4.14 ± 0.09 | 6.94 ± 0.2 | 7.12 ± 0.3 | 7.31 ± 0.4 | 6.81 ± 0.1 | 6.82 ± 0.09 |
| 6 | Amla Fruit Fibers (Soluble + Insoluble) | 16.05 ± 0.6 | 16.94 ± 0.2 | 16.48 ± 0.2 | 15.96 ± 0.2 | 17.40 ± 0.5 | 16.53 ± 0.7 |
| 7 | Amla Soluble Fibers | 20.10 ± 0.7 | 22.18 ± 0.8 | 20.51 ± 0.4 | 20.90. ± 0.8 | 23.72 ± 0.8 | 23.07 ± 0.5 |
| 8 | Amla Insoluble Fibers | 7.12 ± 0.1 | 7.58 ± 0.3 | 7.94 ± 0.6 | 8.19 ± 0.1 | 8.38 ± 0.01 | 8.45 ± 0.1 |
| 9 | Psyllium husk Fiber | 1.05 ± 0.1 | 2.21 ± 0.1 | 2.26 ± 0.1 | 2.28 ± 0.02 | 2.29 ± 0.05 | 3.07 ± 0.1 |
| 10 | Cranberry seed Fiber | 19.74 ± 0.9 | 21.99 ± 0.8 | 24.33 ± 0.3 | 23.95 ± 0.4 | 23.58 ± 0.4 | 23.85 ± 0.7 |
| 11 | Fructooligosaccharide (FOS) | 1.10 ± 0.01 | 3.37 ± 0.09 | 3.12 ± 0.09 | 3.01 ± 0.1 | 3.43 ± 0.09 | 3.34 ± 0.08 |
| 12 | Potato Soluble Starch | 7.45 ± 0.05 | 52.56 ± 0.9 | 54.06 ± 1.1 | 52.29 ± 1.2 | 52.10 ± 1.5 | 54.52 ± 1.1 |

Example 4—Growth Promotional Activity of Plant Based Natural Fiber with *Bacillus coagulans* MTCC 5856

Figure 1B:
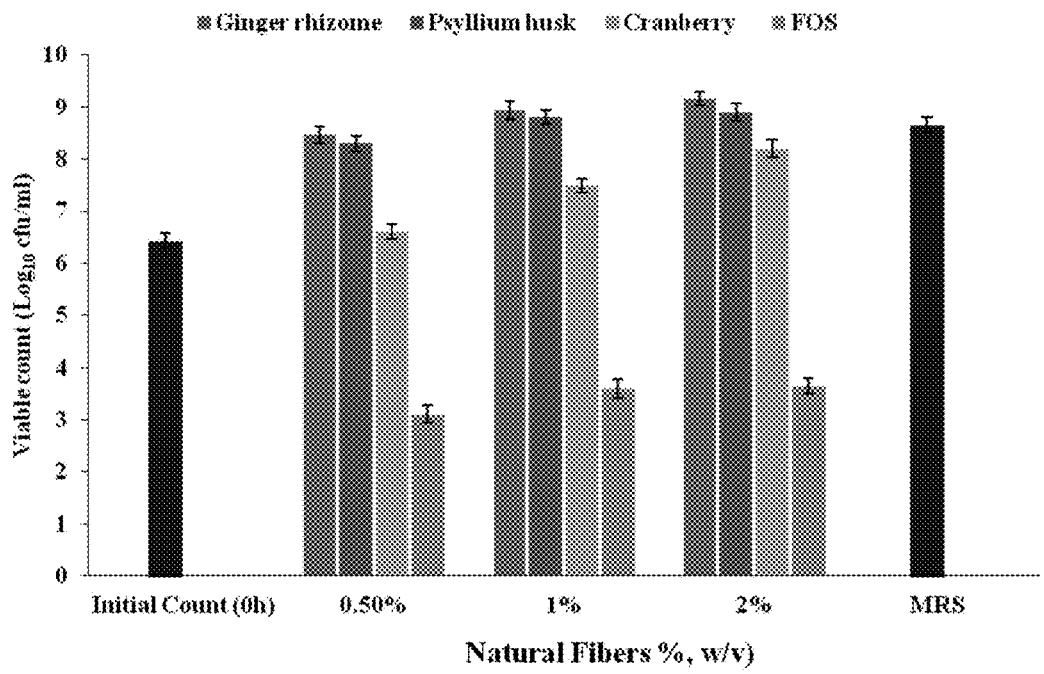
Figure 1C:
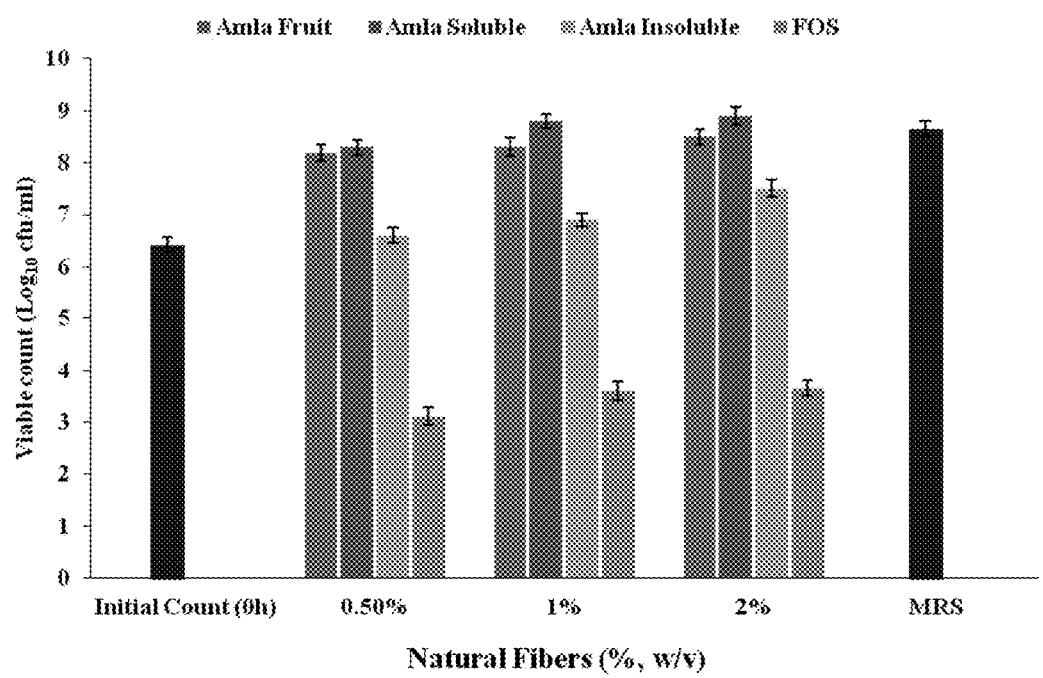
Figure 2A:
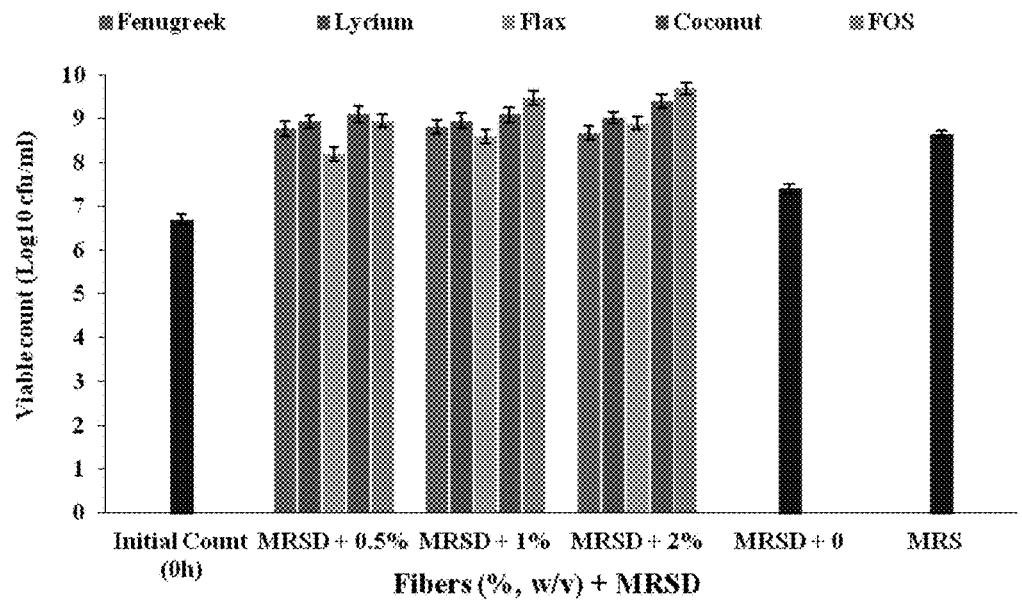
FIGS. 2A, 2B and 2C show the graphical representation of the increase in viable colony count of *Bacillus coagulans* MTCC 5856 in presence of different natural plant fibers (%, w/v) in MRS media (devoid of dextrose) (0.5, 1.0, 2.0%, w/v).
Figure 2B:
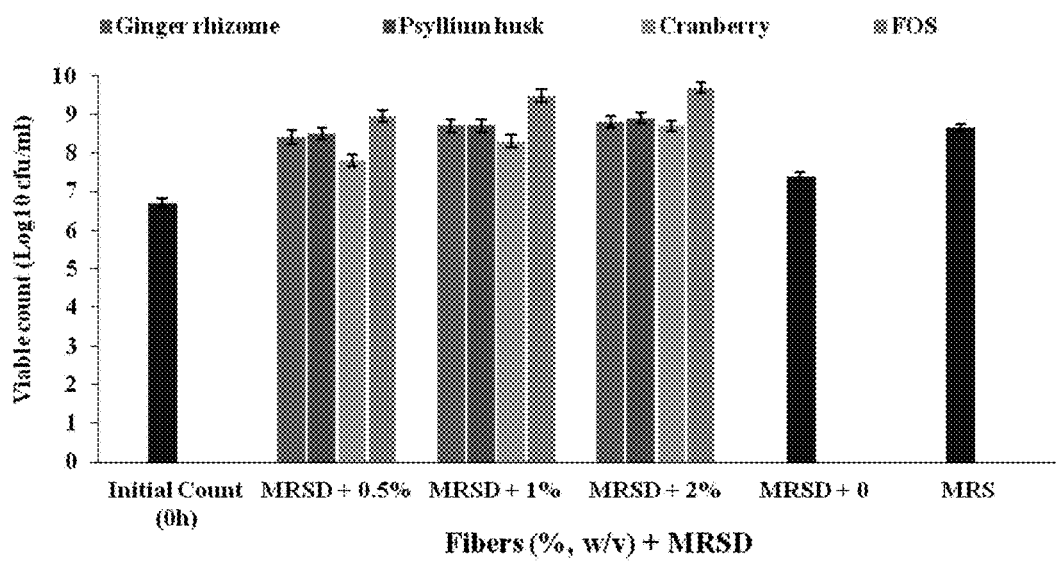
Figure 2C:
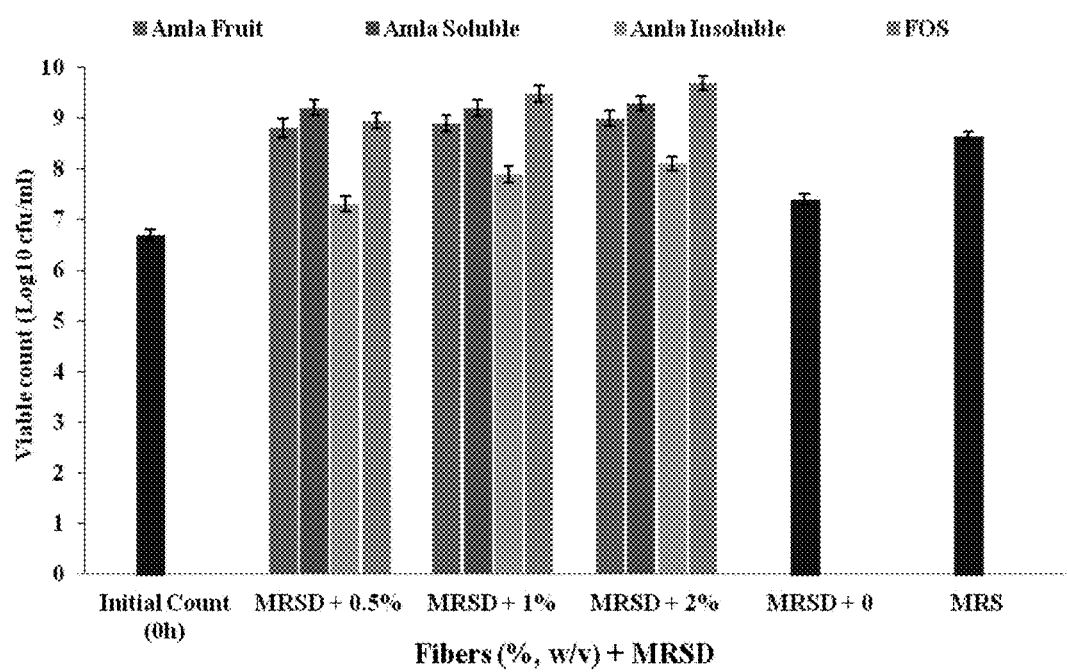

Single isolated colony of *Bacillus coagulans* MTCC 5856 was inoculated into MRS broth (pH 7.0±20; Himedia, Mumbai, India) and incubated at 37° C. with 120 rpm for overnight. Plant based natural fibers alone (0.5, 1.0, 2.0%, w/v), and in MRS media (devoid of dextrose) (0.5, 1.0, 2.0%, w/v) were prepared. MRS broth and MRS (devoid of dextrose) were also prepared separately. Similarly, Fructooligosaccharide (FOS) was also taken in the study as reference control to compare with plant based natural fibers. The final pH of all the media was adjusted to 7.0. Five percent of overnight grown *Bacillus coagulans* MTCC 5856 culture was inoculated to all the flasks and incubated at 37° C. with 100 rpm for 24 h. pH values at 0 h of incubation and after fermentation (24 h) were also recorded. Samples were serially diluted in sterile saline and the viable count was enumerated by plating on glucose yeast extract agar (HiMedia, Mumbai, India) at 0 h and after fermentation (24 h). The plates were incubated at 37° C. for 48 to 72 h. Each analysis was performed in triplicate at two different occasions. Average mean of viable counts are expressed in log 10 cfu/ml (FIGS. 1A, 1B and 1C).

Example 5—Inhibition of *E. coli* Growth

Figure 3:
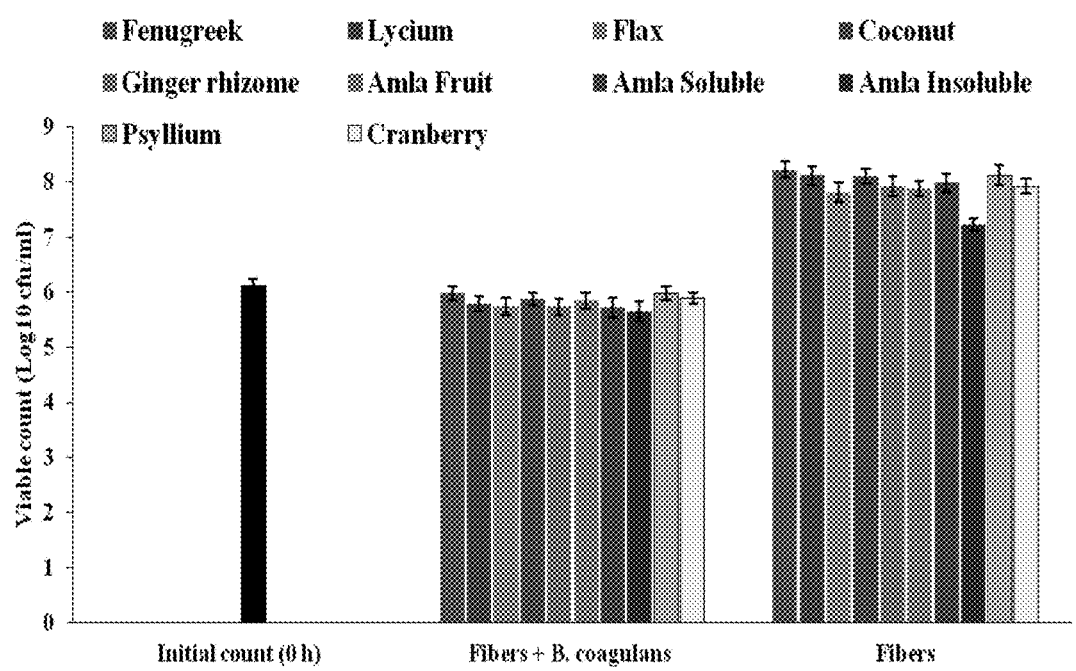
FIG. 3 is the graphical representation of inhibition of *E. coli* ATCC 25922 growth by *B. coagulans* MTCC 5856 when co-cultured in plant based natural fibers as media. Average mean of viable counts are expressed in $\log_{10}$ cfu/ml.

The in-vitro experiment was designed to evaluate the effect of Plant based natural fibers with probiotic bacteria *Bacillus coagulans* MTCC 5856 for the inhibition of Gram negative pathogenic bacteria *E. coli*. Briefly, 2.0 g of plant based natural fibers were added to 100 ml of demineralized water. *Psyllium* husk Fiber and Flax seed fibers were added 0.5 gm to 100 mL of demineralized water due to high gelling property. The pH was adjusted to 7.0±0.2 and autoclaved at 121° C. for 20 min. After sterilization, oxygen reducing enzyme Oxyrase (Oxyrase® for Broth, Oxyrase, Inc, Mansfield, Ohio, USA) was added to each flask. *Bacillus coagulans* MTCC 5856 was grown on glucose yeast extract agar (Himedia, Mumbai, India) and *E. coli* ATCC 25922 was grown on trypticase soya agar (Himedia, Mumbai, India). Single isolated colony of both the cultures was used and the turbidity of the bacterial suspension was adjusted to 0.5 McFarland standards (equivalent to 1.5×108 colony forming units (CFU)/ml). One milliliter of *E. coli* ATCC 25922 was added to flask containing plant based natural fiber. Similarly, in other group 1 ml of *E. coli* ATCC 25922 and 1 ml of *B. coagulans* MTCC 5856 were added to flask containing plant based natural fiber. The flasks were incubated at 37° C. with 100 rpm for 24 h. Samples were serially diluted in sterile saline and the viable count of *E. coli* ATCC 25922 was enumerated by plating on Eosin Methylene Blue Agar (EMB Agar; HiMedia, Mumbai, India) at 0 h and after fermentation (24 h). The plates were incubated at 37° C. for 48 h. Each analysis was performed in triplicate at two different occasions. Average mean of viable counts are expressed in $\log_{10}$ cfu/ml (FIG. 3).

Example 6—Production of SCFA by *Bacillus coagulans* MTCC 5856 Using Plant Based Natural Fibers The in vitro fermentation with the *Bacillus coagulans* MTCC 5856 was carried out by following method described by McBurney and Thompson (McBurney M I and Thompson L U. (1987) Effect of human faecal inoculum on in vitro fermentation variables. Brit J Nutr 58: 233-243) with some modifications. Briefly, 2.0 g of glucose or Plant Based Natural Fibers were added to 100 mL of demineralised water. *Psyllium* husk Fiber and Flax seed fibers were added 0.5 gm to 100 ml of demineralised water due to high gelling property. The pH was adjusted to 7.0±0.2 and autoclaved at 121° C. for 20 min. After sterilization, oxygen reducing enzyme Oxyrase (Oxyrase® for Broth, Oxyrase, Inc, Mansfield, Ohio, USA) was added to each flask, to induce anaerobic conditions. Five percent of overnight grown *Bacillus coagulans* MTCC 5856 culture was inoculated to all the flasks and incubated at 37° C. with gentle shaken rpm for 24 h. The bottles were tightly closed and sealed with parafilm to maintain anaerobic conditions generated by the enzyme supplement. pH values at 0 h of incubation and after fermentation (24 h) were also recorded. One ml of copper sulphate (10 g/L) was added to each sample to inhibit further microbial growth (Sigma, St. Louis, Mo., USA). The analysis of short chain fatty acids in the aforesaid fermentation samples was done adopting the following parameters.

Reagents
1. Diethyl Ether (AR Grade)
2. $H_2SO_4$
3. RO Water
4. Sodium Chloride (AR Grade)

Chromatographic Conditions
Oven:

| Rate | Temperature | Bold time |
|---|---|---|
| Initial | 80° C. | 1.00 minute |
| 8° C./minute | 200° C. | 2.00 minute |

| 1. | Post run temperature | 220° C. |
|---|---|---|
| 2. | Post Time | 5.0 min |
| 3. | Run time | 18.00 min |

Inlet

| Injection Volume | 1 µl |
|---|---|
| Temperature | 250° C. |
| Mode | Split |
| Split ratio | 10:1 |

Column
1. DB-FFAP (Terephthalic acid modified poly ethylene Glycol)
2. Dimensions: 30.00 m×250.00 mm×0.25 µm.
3. Carrier gas:Nitrogen
4. Flow: 1.0 ml/min Detector

| 1. | Type | FID |
|---|---|---|
| 2. | Temperature | 350° C. |
| 3. | Hydrogen Flow | 30.0 ml/min |
| 4. | Air flow | 300.0 ml/min |
| 5. | Make Up Flow | 5.0 ml/min |

Standard Solution Preparation 100.0 mg of each of Fatty acid standard (Acetic acid, Propionic acid and Butyric acid) was weighed accurately in a 100 ml volumetric flask & dissolved in 50.0 mL of water and made up to the mark with water and mixed well (Stock solution). Further, 10.0 mL of the stock solution was diluted to 100.0 mL with water and mixed well to get standard solution. 5 mL of standard solution was subjected to extraction as described herein below.
1. Taken 5 ml of Standard solution/sample.
2. To Standard solution added 5 ml of water with vortexing for 0.5 min.
3. Adjusted pH to 1-1.5 with 3M $H_2SO_4$ with vortexing for 0.5 min.
4. Kept diethyl ether in −20° C. up to 1 hr before adding to the sample/Working Standard.
5. Added 10 ml of diethyl ether with vortexing for 1 min.
6. Added 4 g of Sodium Chloride with vortexing for 1 min.
7. Centrifuged to separate Water Layer & Diethyl Layer
8. Transferred 1.0 mL of Diethyl Ether layer in GC Vial & Injected.

Procedure:

1 µl each of extracted standard solution was injected into the chromatograph in triplicate and recorded the responses of major peaks due to Acetic acid, Propionic acid and Butyric acid. The % Relative Standard Deviation for area of peaks due to Acetic acid, Propionic acid and Butyric acid in triplet injections should not be more than 2.0%. Injected 1.0 µl each of extracted sample solution into the chromatograph. The content of Acetic acid, Propionic acid and Butyric acid was calculated as follows.

$$\text{Content of individual acid in ppm} = \frac{\text{Sample area} \times \text{Std. conc. (ppm)}}{\text{Standard area}}$$

Figure 4:
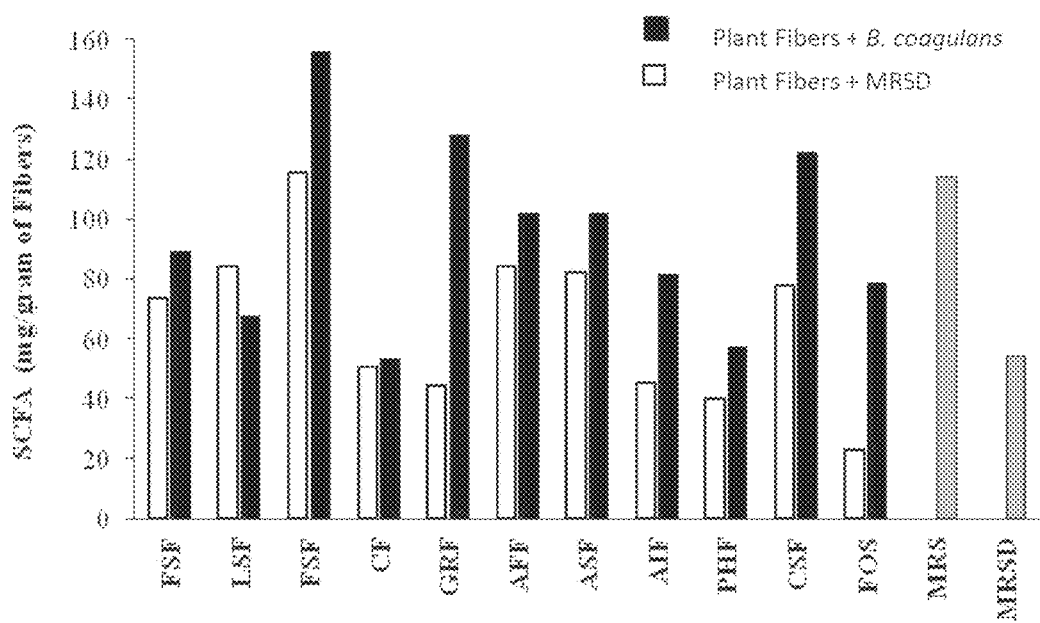
FIG. 4 shows the production of total short chain fatty acid (acetate, butyrate, and propionate) by the *B. coagulans* MTCC 5856 from Fenugreek seed fibers (FSF), *Lycium barbarum* seed fibers (LSF), Flax seed fibers (FLSF), Coconut Fibers (CF), Ginger rhizome fibers (GRF), Amla Fruit Fiber (Soluble+Insoluble) (AFF), Amla Soluble Fibers (ASF), Amla Insoluble Fibers (AIF), *Psyllium* husk Fibers (PHF), Cranberry seed Fibers (CSF), Fructooligosaccharide (FOS), MRS Media (MRS), and MRS Media devoid of Dextrose (MRSD). Average mean of the SCFAs are expressed in mg per gram of fiber.

The results of the chromatographic analysis are presented in FIG. 4 and represented herein below as Tables 4 and 5. In Table 4 it may be noted that the production (mg/gram of fiber) of short chain fatty acid (Acetate, Propionate and Butyrate) was from plant based natural fibers as a sole nutritional source in vitro batch-culture fermentation with *B. coagulans* MTCC 5856. FOS was used as reference control in the study.

In Table 5 it may be noted that the production (mg/gram if fiber) of short chain fatty acid (acetate, propionate and butyrate) was from plant based natural fibers along with other nutrients in vitro batch-culture fermentation with *B. coagulans* MTCC 5856. In MRS media dextrose was replaced by plant based natural fibers for the production of SCFA. FOS was used as reference control in the study. MRS media and Media devoid of Dextrose (MRSD) were also taken to compare for the production of the study.

TABLE 4

| S. No. | Plant Based Natural Fibers (alone) | Short Chain Fatty Acids (mg/gram of Fibers) | | |
|---|---|---|---|---|
| | | Acetate | Butyrate | Propionate |
| 1 | Fenugreek seed fibers | 69.79 | 3.36 | 0.27 |
| 2 | *Lycium barbarum* seed fibers | 77.18 | 6.56 | 0.24 |
| 3 | Flax seed fibers | 109.5 | 5.93 | 0.27 |
| 4 | Coconut Fibers | 49.39 | 0.96 | 0.14 |
| 5 | Ginger rhizome fibers | 1.62 | 0.20 | 42.35 |
| 6 | Amla Fruit Fiber (Soluble + Insoluble) | 3.87 | 0.30 | 79.99 |
| 7 | Amla Soluble Fibers | 5.50 | 0.23 | 76.55 |
| 8 | Amla Insoluble Fibers | 1.05 | 0.25 | 44.10 |
| 9 | Psyllium husk Fibers | 1.70 | 0.14 | 38.11 |
| 10 | Cranberry seed Fibers | 8.64 | 0.225 | 69.07 |
| 11 | Fructooligosaccharide (FOS) | 1.07 | 0.07 | 21.61 |

TABLE 5

| S. No. | Plant Based Natural Fibers along with MRS Media devoid of dextrose | Short Chain Fatty Acids (mg/gram of Fibers) | | |
|---|---|---|---|---|
| | | Acetate | Propionate | Butyrate |
| 1 | Fenugreek seed fibers | 84.67 | 3.68 | 0.97 |
| 2 | *Lycium barbarum* seed fibers | 61.05 | 5.41 | 0.75 |
| 3 | Flax seed fibers | 146.86 | 7.52 | 1.43 |

TABLE 5-continued

| S. No. | Plant Based Natural Fibers along with MRS Media devoid of dextrose | Short Chain Fatty Acids (mg/gram of Fibers) | | |
|---|---|---|---|---|
| | | Acetate | Propionate | Butyrate |
| 4 | Coconut Fibers | 51.91 | 1.01 | 0.51 |
| 5 | Ginger rhizome fibers | 118.72 | 7.90 | 1.32 |
| 6 | Amla Fruit Fiber (Soluble + Insoluble) | 94.11 | 6.46 | 1.06 |
| 7 | Amla Soluble Fibers | 90.99 | 9.37 | 1.24 |
| 8 | Amla Insoluble Fibers | 79.10 | 1.70 | 0.38 |
| 9 | Psyllium husk Fibers | 53.24 | 3.23 | 0.56 |
| 10 | Cranberry seed Fibers | 110.89 | 9.58 | 1.69 |
| 11 | Fructooligosaccharide (FOS) | 73.96 | 4.30 | 0.24 |
| 12 | MRS Media | 113.07 | 1.04 | 0.05 |
| 13 | MRS Media devoid of Dextrose (MRSD) | 50.36 | 1.17 | 0.16 |

Example 7—Method of Preparing Turmeric Starch Fibers

Turmeric starch (brand name STARMERIC™-obtained from the spent material resulting from the extraction of curcuminoids from the rhizomes of Curcuma longa), was procured from the phytochemistry department of the Sami Labs Limited [R&D arm of Sabinsa Corporation, N.J. USA] and was used in the following experiments.

Example 8—Acid and Enzymatic Hydrolysis

The enzymatic hydrolysis procedure was carried out based on Oku et al. 1984. Journal of Nutrition 114, 1574-1581). 100 mg of Pancreatin 4xUSP (Sigma) was dissolved in 100 ml of phosphate buffer (50 mM; pH 7.0). Further, Turmeric starch (2 gm) was added to the above pancreatin solution and incubated at 37±1° C. with 100 rpm for 180 min. Samples were taken at 0, 30, 60, 90, 120 and 180 min. FOS was also taken in the study as reference to compare with Turmeric starch and potato starch was taken as positive control. The increase in reducing sugar was measured with a Dinitrosalicylate reagent.

The enzymatic hydrolysis was performed as per the procedure described in Nilsson and Bjorck 1988. Journal of Nutrition 118, 1482-1486. The Turmeric starch (2 gm) was added to 100 ml of HCl (0.10 M) and incubated at 37±1° C. with 100 rpm for 180 min. Samples were taken at 0, 30, 60, 90, 120 and 180 min. Fructooligosaccharide (FOS; Tata Chemicals, India) was also taken in the study as reference to compare with Turmeric starch and starch (Potato soluble starch: HiMedia, Mumbai, India) was taken as positive control. The increase in reducing sugar was measured with a Dinitrosalicylate reagent Acid and enzymatic hydrolysis were performed for the turmeric starch to determine its non-digestibility in human digestive system. An in-vitro experiment was performed to mimic the human digestive system for the acid (HCl 0.1M, pH 1.4) and enzymatic hydrolysis (pancreatin contain mixture of amylase, lipase and protease from porcine) of fiber. FOS was taken as reference control for fiber and starch was taken as positive control for its digestibility under in vitro condition.

Figure 5:
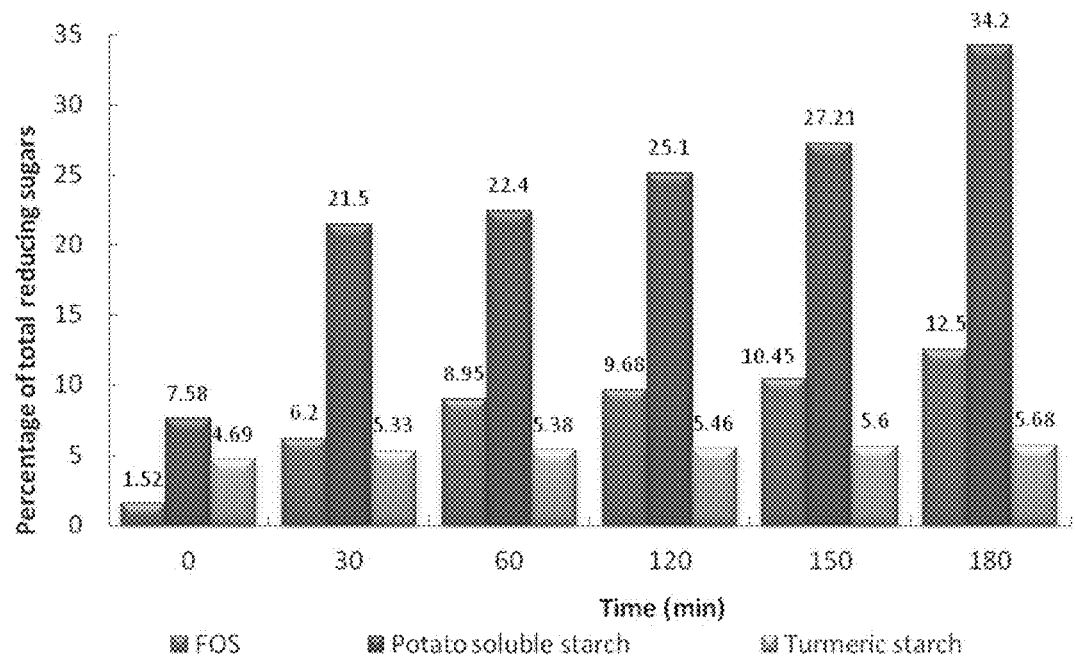
FIG. 5 shows the graphical representation of the acid hydrolysis of turmeric starch.
Figure 6:
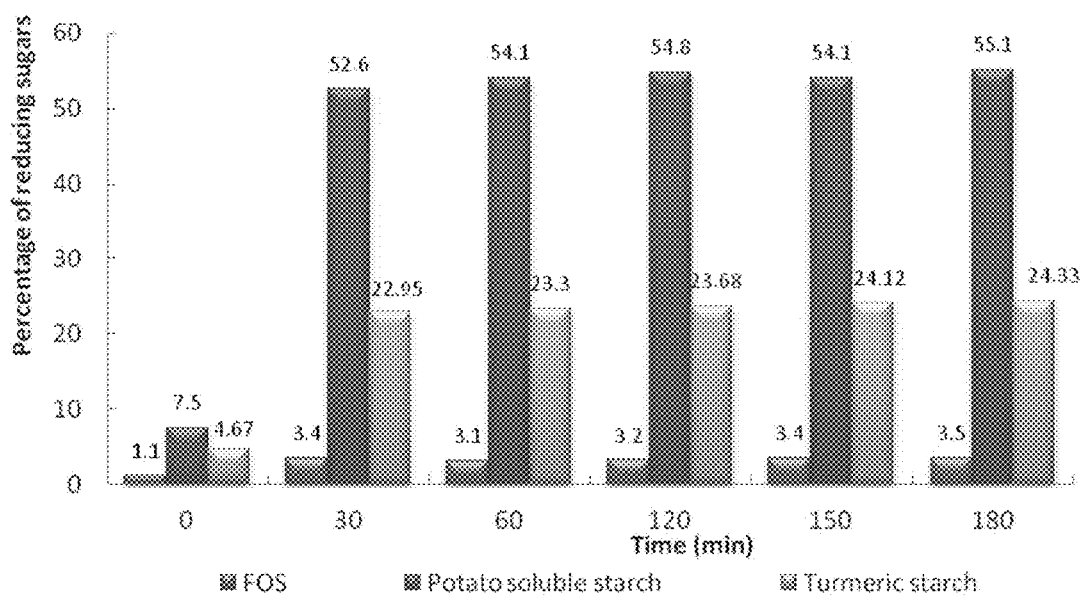
FIG. 6 shows the graphical representation of the Porcine pancreatic enzymatic hydrolysis of turmeric starch.

In the acid and enzyme hydrolysis, potato soluble starch showed 14% and 45% increase in total reducing sugar within 30 min and were found to remain in the range of 27% and 47% increase in total reducing sugar upto 180 min respectively. Turmeric starch showed 18.0% increase in total reducing sugar within 30 min and was found to remain in the range of 19.66% increase in total reducing sugar up to 180 min when hydrolyzed by pancreatic enzymes (FIGS. 5 & 6).

The results suggest that turmeric starch was partially digested by enzymatic treatment. The total carbohydrate in the turmeric starch was 58% and the initial total reducing sugar was 4.67%. After enzymatic hydrolysis, there was an increase in total reducing sugar by 24.33% which resulted in 39.33% digestibility of turmeric starch. Therefore, it can be concluded that turmeric starch contains about 60% of enzymatically resistant starch. The in-vitro study suggested that turmeric starch had non digestibility for acid and partial digestibility to porcine pancreatic enzymes which could be used as a plant fiber for prebiotic application.

Example 9—Growth Promotional Activity of Turmeric Starch with Bacillus coagulans MTCC 5856

Figure 7:
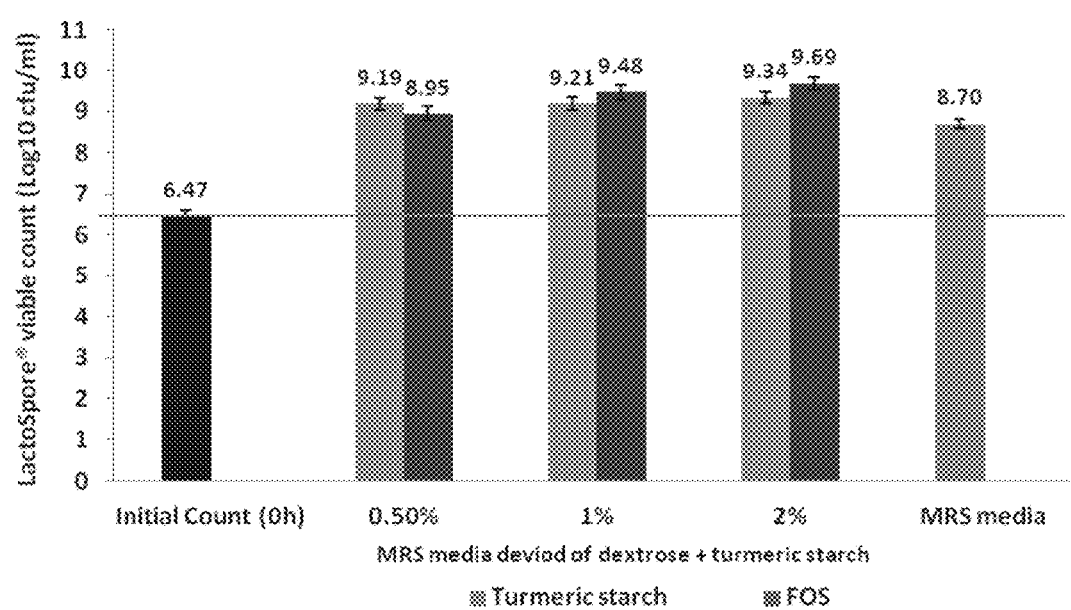
FIG. 7 show the graphical representation of the increase in viable colony count of *Bacillus coagulans* MTCC 5856 in presence of turmeric starch (%, w/v) in MRS media (devoid of dextrose) (0.5, 1.0, 2.0%, w/v).

A single isolated colony of Bacillus coagulans MTCC 5856 was inoculated into MRS broth (pH 6.0; Himedia) and incubated in shaker at 37±1° C., 120 rpm overnight. To evaluate the growth of Bacillus coagulans MTCC 5856 using turmeric starch as carbon source, MRS media was used to evaluate the growth of Bacillus coagulans MTCC 5856 by replacing the dextrose with 2.5 g/L, 5 g/L, 7.5 g/L, 10 g/L of turmeric starch and 2.5 g/L, 5 g/L, 10 g/L dextrose used as control in different set of experiments. MRS with Parameters like pH, OD (600 nm), Sporulation, Total viable count (TVC) was determined by serial dilution using Glucose Yeast Extract agar (Himedia) at 0 h and after fermentation (48 h). Total carbohydrate was quantified by Anthrone method. Viable count was determined by pour plate method using GYE agar media. Turmeric starch was found to be suitable for the growth of B. coagulans MTCC 5856 as the sole carbon source. However, FOS was slightly better than turmeric starch for enhancing the viable count of B. coagulans MTCC 5856 at 1.0 and 2.0%, but at 0.5% concentration, B. coagulans MTCC 5856 viable count was better compare to FOS (FIG. 7). Hence, turmeric starch could be further explored as a prebiotic.

Example 10—Production of SCFA by Bacillus coagulans MTCC 5856 Using Turmeric Starch The in vitro fermentation of turmeric starch with the Bacillus coagulans MTCC 5856 was carried out and the short chain fatty acids were measured by the method described in Example 6. The results of SCFA produced by Bacillus coagulans MTCC 5856 in the presence of turmeric starch is tabulated in Table 6.

TABLE 6

Production of Short Chain fatty acids by Bacillus coagulans MTCC 5856 in presence of turmeric starch

| S. No. | Samples | Time (h) | Short chain fatty acids (mg/g of fibres) | | |
|---|---|---|---|---|---|
| | | | Acetic acid | Butyric acid | Propionic acid |
| 1 | Turmeric Starch (2.5 g/L) | 24 | 442.3 | 10.2 | 3.8 |
| | | 48 | 664.0 | 8.6 | 0.02 |
| | | 72 | 628.0 | 6.5 | 0.6 |
| 2 | Turmeric Starch (5.0 g/L) | 24 | 338.2 | 5.7 | 2.0 |
| | | 48 | 386.6 | 5.3 | 0.1 |
| | | 72 | 593.4 | 2.8 | 0.3 |

TABLE 6-continued

Production of Short Chain fatty acids by *Bacillus coagulans* MTCC 5856 in presence of turmeric starch

| S. No. | Samples | Time (h) | Short chain fatty acids (mg/g of fibres) | | |
|---|---|---|---|---|---|
| | | | Acetic acid | Butyric acid | Propionic acid |
| 3 | Turmeric Starch (7.5 g/L) | 24 | 188.1 | 3.8 | 1.3 |
| | | 48 | 546.8 | 1.3 | 0.1 |
| | | 72 | 596.8 | 1.7 | 0.2 |
| 4 | Turmeric Starch (10.0 g/L) | 24 | 182.7 | 7.0 | 0.8 |
| | | 48 | 702.8 | 3.7 | 0.1 |
| | | 72 | 643.7 | 2.6 | 0.2 |
| 5 | Dextrose (10.0 g/L) | 24 | 134.3 | 1.7 | 1.0 |
| | | 48 | 428.0 | 5.5 | 1.2 |
| | | 72 | 472.1 | 1.4 | 1.0 |

Acetate was found to be the highest SCFA produced by *Bacillus coagulans* MTCC 5856 while fermenting turmeric starch and also dextrose. However, while fermenting starch at various concentrations; the production of acetate was significantly higher than the dextrose group. Butyric acid and propionic acid production by *Bacillus coagulans* MTCC 5856 was also observed to be relatively higher while fermenting turmeric starch, when compared to the dextrose group. A concentration and time dependant production of SCFA by *Bacillus coagulans* MTCC 5856 was noticed while fermenting turmeric starch. In conclusion, based on the in-vitro studies, turmeric starch holds the potential of a prebiotic fiber.

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A method comprising co-culturing *Bacillus coagulans* MTCC 5856 with turmeric starch.

2. The method according to claim 1, wherein the viable colony count of *Bacillus coagulans* MTCC 5856 is increased by the co-culturing method.

3. A method of producing short chain fatty acids, by co-culturing *Bacillus coagulans* MTCC 5856 with turmeric starch under fermenting conditions to produce short chain fatty acids.

4. The method according to claim 3, wherein the short chain fatty acids are one or more selected from the group consisting of acetic acid, propionic acid, and butyric acid.

5. The method according to claim 3, wherein the *Bacillus coagulans* MTCC 5856 and the turmeric starch are fermented under anaerobic conditions.

* * * * *